(12) United States Patent
Ng et al.

(10) Patent No.: US 7,700,126 B2
(45) Date of Patent: Apr. 20, 2010

(54) TROPOELASTIN-BASED PROTOELASTIN BIOMATERIALS

(76) Inventors: Martin Kean Chong Ng, 24 The Grove, Mosman, New South Wales (AU) 2088; Anthony Steven Weiss, 235 Rainbow Street, NSW 2031, Randwick (AU); Steven Garry Wise, 17 Graham Place, Picnic Point, NSW 2213, New South Wales, Sydney (AU)

( * ) Notice: Subject to any disclaimer, the term of this patent is extended or adjusted under 35 U.S.C. 154(b) by 0 days.

(21) Appl. No.: 11/864,006

(22) Filed: Sep. 28, 2007

(65) Prior Publication Data

US 2008/0107708 A1 May 8, 2008

Related U.S. Application Data

(60) Provisional application No. 60/848,056, filed on Sep. 29, 2006.

(51) Int. Cl.
*A61F 2/00* (2006.01)
(52) U.S. Cl. .................. 424/423; 530/300; 530/350; 424/9.3; 435/7.1; 435/69.1
(58) Field of Classification Search ................ None
See application file for complete search history.

(56) References Cited

U.S. PATENT DOCUMENTS

| | | | | |
|---|---|---|---|---|
| 6,232,458 | B1 * | 5/2001 | Weiss et al. ............. | 536/23.5 |
| 7,193,043 | B1 * | 3/2007 | Weiss ..................... | 530/350 |
| 7,258,988 | B2 | 8/2007 | Yang et al. | |

FOREIGN PATENT DOCUMENTS

| | | |
|---|---|---|
| WO | WO 94/14958 | 7/1994 |
| WO | WO 98/34563 | 8/1998 |
| WO | WO 99/03886 | 1/1999 |
| WO | WO 99/45894 | 9/1999 |
| WO | WO 00/50068 | 8/2000 |
| WO | WO 2006/091775 | 8/2006 |
| WO | WO 2007/048115 | 4/2007 |

OTHER PUBLICATIONS

Wells, Biochemistry, vol. 29, pp. 8509-8517, 1990.*
Li, et al., "Electrospun protein fibers as matrices for tissue engineering", *Biomaterials*, 26(30):5999-6008 (2005).
Abraham and Carnes, "Isolation of a cross-linked dimer of elastin," *J. Biol. Chem*, 253, 7993-5(1978).
Bashir et al., "Characterization of the complete human elastin gene. Delineation of unusual features in the 5'-flanking region," *J Biol Chem*, 264:8887-91(1989).
Bilek et al. "Functional attachment of horse radish peroxidase to plasma-treated surfaces," In *Smart Materials III*, vol. 5648 (Ed, Wilson, A. R.) SPIE, pp. 62-67(2004).
Bilek et al. "Plasma-based ion implantation utilising a cathodic arc plasma," *Surface and Coatings Technology*, 156:136-142(2002).

Broekelmann et al., "Tropoelastin interacts with cell-surface glycosaminoglycans via its COOH-terminal domain," *J. Biol. Chem.* 280(49):40939-47(2005).
Buttafoco et al., "Electrospinning of collagen and elastin for tissue engineering applications," *Biomaterials*, 27: 724-34 (2006).
Clarke et al. "Coacervation is promoted by molecular interactions between the PF2 segment of fibrillin-1 and the domain 4 region of tropoelastin," *Biochemistry* 44(30):10271-81 (2005).
Cox et al., "Coacervation of alpha-elastin results in fiber formation," *Biochim Biophys Acta*, 317:209-13(1973).
Cullberg et al., "Population modelling of the effect of inogatran, at thrombin inhibitor, on ex vivo coagulation time (APTT) in healthy subjects and patients with coronary artery disease," *Brit. J. Cli. Pharmacol.*, 51, 71-91(2001).
Fitzgibbon et al., "Coronary bypass graft fate and patient outcome: angiographic follow-up of 5,065 grafts related to survival and reoperation in 1,388 patients during 25 years," *J. Am. Coll. Cardiol.*, 28: 616-626(1996).
Gan et al. "Etching and structural changes in nitrogen plasma immersion ion implanted polystyrene films," *Nuclear Instruments and Methods in Physics Research B*, 247. 254-260(2006).
Nosworthy et al. "The attachment of catalase and poly-I-lysine to plasma immersion ion implantation-treated polyethylene," *Acta Biomater*, 3:695-704(2007).
Parks and Deak, "Tropoelastin heterogeneity: implications for protein function and disease," *Am. J. Respir. Cell Mol. Biol.*, 2(5):399-406(1990).
Phaneuf et al "Modification of polyethylene terephthalate (Dacron) via denier reduction: effects on material tensile strength, weight, and protein binding capabilities," *Journal of Applied Biomaterials*, 6:289-99(1995).
Phaneuf et al. "Modification of polyethylene terephthalate (Dacron) via denier reduction: effects on material tensile strength, weight, and protein binding capabilities," *J. App. Biomater.* 6, 289-99 (1995).
Rich and Foster, "Isolation of tropoelastin a from lathyritic chick aortae," *Biochem. J.* 217:581-4(1984).
Rodgers and Weiss "Integrin alpha v beta 3 binds a unique non-RGD site near the C-terminus of human tropoelastin," *Biochimie* 86:173-178(2004).

(Continued)

*Primary Examiner*—Hope A Robinson
(74) *Attorney, Agent, or Firm*—Pabst Patent Group LLP

(57) ABSTRACT

Biocompatible materials suitable for use in vascular applications have been engineered, combining human recombinant tropoelastin with other synthetic or natural biomaterials to form protoelastin. The materials can be in the form of elastin films on metal, bone, ceramic or polymer substrates, laminates of alternating polymer and elastin, blends of polymer and elastin, or elastin crosslinked with or tethered to polymer. The flexibility in engineering and design makes protoelastin biomaterials suited not only to the production of conduits but any number of other vascular applications that require blood contacting surfaces. Tropoelastin and the subsequently engineered biomaterial protoelastin provide the opportunity to satisfy a large unmet need for a biocompatible material adaptable enough to meet a range of diverse vascular uses. These are mechanically stable, elastic, strong and biocompatible (i.e., not thrombogenic and promoting adhesion of cells, especially human endothelial cells.

22 Claims, 8 Drawing Sheets

OTHER PUBLICATIONS

Rodgers and Weiss, "Integrin alpha v beta 3 binds a unique non-RGD site near the C-terminus of human tropoelastin," *Biochimie*, 86:173-178(2004).

Sandberg and Wolt, "Production and isolation of soluble elastin from copper-deficient swine," *Methods in Enzymology*, 82 Pt A, 657-65(1982).

Santerre et al., "Understanding the biodegradation of polyurethanes: from classical implants to tissue engineering materials," *Biomaterials*, 26: 7457-70(2005).

Starcher et al., "Elastin coacervate as a matrix for calcification," *Biochim Biophys Acta*, 310:481-6(1973).

Stitzel et al., "Controlled fabrication of a biological vascular substitute," *Biomaterials*, 27:1088-94(2006).

Stone et al., "Building Elastin. Incorporation of recombinant human tropoelastin into extracellular matrices using nonelastogenic rat-1 fibroblasts as a source for lysyl oxidase," *Amer. J. Respir. Cell .Mol. Biol.* 24:733-739(2001).

Tai et al., "Compliance properties of conduits used in vascular reconstruction," *Br. J. Surg.* 87(11):1516-24(2000).

Teo and Ramakrishna "A review on electrospinning design and nanofibre assemblies," *Nanotechnology*, 17:R89-R106(2006).

Teo, et al. "Porous tubular structures with controlled fibre orientation using a modified electrospinning method," *Nanotechnology*, 16:918-924(2005).

Toonkool et al., "Thermodynamic and hydrodynamic properties of human tropoelastin. Analytical ultracentrifuge and pulsed field-gradient spin-echo NMR studies," *J. Biol. Chem.* 276, 28042-50(2001).

Visconti et al., "Codistribution analysis of elastin and related fibrillar proteins in early vertebrate development," *Matrix Biol.*, 22:109-21 (2003).

Wagenseil et al., "Effects of elastin haploinsufficiency on the mechanical behavior of mouse arteries," *Amer. J. Physiol.—Heart and Circulation Physiology*, 289:H1209-17(2005).

Wu et al. "Glycosaminoglycans mediate the coacervation of human tropoelastin through dominant charge interactions involving lysine side chains," *J. Biol. Chem.* 274:21719-24(1999).

Xue and Greisler, "Biomaterials in the development and future of vascular grafts," *J. Vasc. Sur.* 37:472-80(2003).

Goldman et al., "Long-term patency of saphenous vein and left internal mammary artery grafts after coronary artery bypass surgery: results from a Department of Veterans Affairs Cooperative Study," *J. Am. Coll. Cardiol.* 44:2149-56(2004).

Grabarek and Gergely "Zero-length crosslinking procedure with the use of active esters," *Anal Biochem.* 185(1):131-5(1990).

Gunatillake et al., "Poly(dimethylsiloxane)/poly(hexamethylene oxide) mixed macrodiol based polyurethane elastomers. I. Synthesis and properties," *J. App. Poly. Sci.* 76:2026-2040(2000).

Hinds et al., "Development of a reinforced porcine elastin composite vascular scaffold," *J. Biomed. Mater. Res. Part A*, 77:458-69(2006).

Indik et al., "Production of recombinant human tropoelastin: characterization and demonstration of immunologic and chemotactic activity," *Arch Biochem Biophys*, 280:80-6(1990).

Kagan and Sullivan, "Lysyl oxidase: preparation and role in elastin biosynthesis," *Methods in Enzymology*, 82:637-650(1982).

Kannan et al., "Current status of prosthetic bypass grafts: a review," *J. Biomed. Mate. Res. B Applied Biomaterials*, 74:570-81(2005).

Martin et al. "Total synthesis and expression in *Escherichia coli* of a gene encoding human tropoelastin," *Gene*, 154:159-166(1995).

Martin et al., "Total synthesis and expression in *Escherichia coli* of a gene encoding human tropoelastin," *Gene* 154:159-66(1995).

Mecham and Foster, "Characterization of insoluble elastin from copper-deficient pigs. Its usefulness in elastin sequence studies," *Biochimica et Biophysica Acta*, 577:147-58(1979).

Mithieux et al., "Elastin," *Adv. In Protein Chemistry*, 70:437-61(2005).

* cited by examiner

SEQUENCE LISTING

```
<160> NUMBER OF SEQ ID NOS: 2

<210> SEQ ID NO 1
<211> LENGTH: 16
<212> TYPE: PRT
<213> ORGANISM: Homo Sapiens
<220> FEATURE:
<221> NAME/KEY: MISC_FEATURE
<222> LOCATION: (1)..(16)
<223> OTHER INFORMATION: Domain 36 of human tropoelastin

<400> SEQUENCE: 1

Ile Phe Pro Gly Ala Cys Leu Gly Lys Ala Cys Gly Arg Lys Arg Lys
1               5                   10                  15

<210> SEQ ID NO 2
<211> LENGTH: 4
<212> TYPE: PRT
<213> ORGANISM: Homo Sapiens
<220> FEATURE:
<221> NAME/KEY: MISC_FEATURE
<222> LOCATION: (1)..(4)
<223> OTHER INFORMATION: C-terminus of human tropoelastin

<400> SEQUENCE: 2

Arg Lys Arg Lys
1
```

TROPOELASTIN-BASED PROTOELASTIN BIOMATERIALS

CROSS-REFERENCED TO RELATED APPLICATION

This application claims priority to U.S. Ser. No. 60/848,056 filed Sep. 29, 2006 and where permissible is incorporated herein in its entirety.

FIELD OF THE INVENTION

This application generally relates to improved elastin based biomaterials prepared using recombinant human tropoelastin, which are characterized by increased biocompatibility and mechanical and tensile strength.

BACKGROUND OF THE INVENTION

Despite the increasing incidence of cardiovascular disease, there are few effective biomaterials currently available for clinical vascular applications. Currently available synthetic biomaterials such as polyethylene terephthalate have a range of vascular applications including endovascular grafting, heart valve replacement, vascular/myocardial patches and vascular closure devices, but it is their poor performance as vascular surgical conduits that exemplifies their deficiencies.

Autologous veins or arteries are preferentially used due to their superior performance and patency, but in at least 30% of patients, these grafts are unavailable due to prior use or disease (Goldman et al., (2004) *J. Am. Coll. Cardiol.* 44, 2149-56). The early patency of vein graphs can be maximized by the surgeon, though long term failure is unavoidable, resulting mainly from uncontrolled smooth muscle cell proliferation (Fitzgibbon et al., 1996) *J. Am. Coll. Cardiol.*, 28, 616-626). In cases where autologous arterial or venous grafts are unusable or not available, the two leading synthetic materials for both surgical and endovascular implantation are polyethylene terephthalate (DACRON®) and expanded polytetrafluoroethylene (ePTFE). Both polymers perform well in high flow vessels with diameters greater than 6 mm, but neither is suitable for small diameter (less than 4 mm) grafts (Xue and Greisler, 2003) *J. Vasc. Sur.* 37, 472-80). Both synthetic graft types produce an unfavourable immune response, are highly thrombogenic and do not adequately mimic the compliance of native vessels. Incomplete endothelialization leads to chronic inflammation and hyperplasia (Kannan et al., (2005), *J. Biomed. Mate. Res. B Applied Biomaterials*, 74, 570-81). This poor performance has been attributed both to the mismatched physical properties of the synthetic graft as well as the intrinsic haemocompatibility of the graft surface (Tai et al., 2000). For example, the tensile strength of Dacron (170-180 MPa) and ePTFE (14 MPa) (Kannan et al., 2005) is substantially greater than those observed for arterial and venous material (1-3 MPa) (Black, (1998) *Handbook of biomaterial properties*, Springer).

The inadequacy of existing polymeric graft materials has constantly been challenged by the development of new materials, particularly those with more favourable physical properties. An important class of non-biodegradable polymers proposed for vascular graft use are polyurethane elastomers, which exhibit good hemocompatibility and have excellent mechanical properties (Gunatillake et al., (2000) *J. App. Poly. Sci.* 76, 2026-2040). The wider use of polyurethane biomaterials has been limited, however, by questions surrounding long-term stability of implanted materials. The combined susceptibility of polyurethanes to hydrolysis, cracking, enzymatic degradation, calcification and corrosion to varying degrees depending on the formulation (Santerre et al., (2005), *Biomaterials,* 26, 7457-70) has led to these doubts regarding biostability and bi-product toxicity. The problems faced by polyurethane biomaterials are common to this field and have prevented any strong competition to DACRON® and ePTFE from emerging. It is clear then, that a large unmet need for a more biocompatible, durable and clinically effective synthetic biomaterial remains.

Elastin has frequently been used in combination with other supporting components. Elastin, digested from animal sources has been combined with gelatin, collagen (Buttafoco et al., (2006) *Biomaterials,* 27, 724-34) and polymers such as poly(lactide-co-glycolide) (Stitzel et al., (2006) *Biomaterials,* 27, 1088-94) using electrospinning and producing fibers with improved tensile characteristics. Elastin from porcine arteries has also been used as the scaffold for a graft material, reinforced by physically wrapping the construct with small intestinal submucosa (essentially decellularized collagen) (Hinds et al., (2006) *J. Biomed. Mater. Res. Part A,* 77, 458-69). Tensile strengths of 1-2 MPa have been reached using these approaches. These materials however, are limited not only by the difficulties associated with the quality and supply of animal elastin but also the likely thrombogenicity of the supporting material.

It is therefore an object of the present invention to provide materials which are suitable for vascular application that are biocompatible and not thrombogenic or having very low thrombogenicity.

It is a further object of the present invention to provide such materials which also have mechanical strength and elasticity that are desirable for vascular applications.

SUMMARY OF THE INVENTION

Biocompatible materials suitable for use in vascular applications have been engineered, combining human recombinant tropoelastin with other synthetic or natural biomaterials to form protoelastin. The materials can be in the form of elastin films on metal, bone, ceramic or polymer substrates, laminates of alternating polymer and elastin, blends of polymer and elastin, or elastin crosslinked with or tethered to polymer or metal. These protoelastin biomaterials can include other extracellular matrix materials such as fibrillins, crosslinked glycosaminoglycans ("GAGs"), collagen and collagen derivatives, and other natural materials, which may in some cases be the polymer substrate or blend.

The tropoelastin is produced by expression of the recombinant nucleic acid molecule encoding tropoelastin or a derivative or alternatively spliced form thereof. The biomaterial may include one or more forms of tropoelastin or a variant or derivative thereof. A preferred splice variant is tropoelastin not including domain 26A. Another preferred derivative includes a fragment of the tropoelastin that encompasses the region around the C-terminus, encoded by the last exon. Other desirable portions of the tropoelastin include the non-RGD integrin binding region. The tropoelastin is then crosslinked, blended, and/or tethered to a material to produce the protoelastin. The resulting materials have applications in tissue engineering, as vascular conduits or in repair thereof. The flexibility in engineering and design makes protoelastin biomaterials suited not only to the production of conduits but any number of other vascular applications that require blood contacting surfaces. The materials are highly biocompatible, not eliciting a foreign body response. Synthetic elastin (crosslinked tropoelastin) does not affect the clotting time of normal citrated plasma, compared to saline (negative control) and Kaolin (positive control).

Tropoelastin and the subsequently engineered biomaterial protoelastin provide the opportunity to satisfy a large unmet need for a biocompatible material adaptable enough to meet a range of diverse vascular uses. These are mechanically stable, elastic, strong and biocompatible (i.e., not thrombogenic and promoting adhesion of cells, especially human endothelial cells.

DETAILED DESCRIPTION OF THE INVENTION

I. Definitions

Figure 1A:
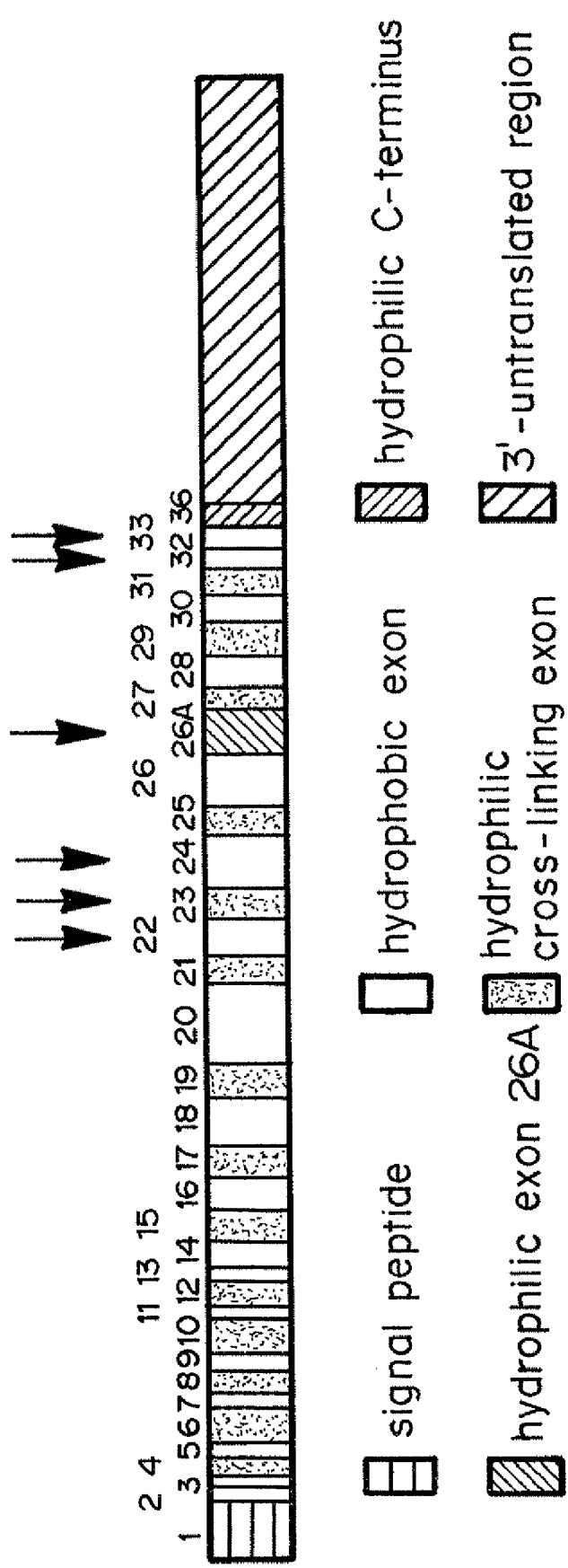
FIG. 1A is a schematic of the arrangement of exons in the human elastin gene. The figure highlights the alternating hydrophobic and hydrophilic exons that characterize much of the structure. Domains 26A and 26 are not easily characterized and are separately noted. Exons subject to alternate splicing, giving rise to multiple tropoelastin isoforms, are marked with an arrow. Figure from Vrhovski and Weiss 1998.

Tropoelastin is the protein that is expressed and post-translationally modified from the gene encoding elastin, prior to cross-linking to form elastin. Martin et al. (1995) Gene, 154, 159-166, details the making of the synthetic gene and subsequent expression of synthetic human elastin (SHEL). A used herein, "tropoelastin" encompasses full length tropoelastin, isoforms of tropoelastin, genetically engineered tropoelastin constructs, fragments and derivatives of tropoelastin, unless otherwise specified.

Full Length tropoelastin refers to the full protein sequence expressed from the human elastin gene. Given that exon 1 encodes a signal peptide that is subsequently cleaved, this form would span from domain 2 to domain 36 (Domains 2, 3, 4, 5, 6, 7, 8, 9, 10, 11, 12, 13, 14, 15, 16, 17, 18, 19, 20, 21, 22, 23, 24, 25, 26, 26A, 27, 28, 29, 30, 31, 32, 33 and 36). Notably, human tropoelastin lacks domains 34 and 35.

Fragments of tropoelastin include any isoforms or constructs expressed from genetically engineered nucleic acid molecules. The following are representative isoforms and fragments. Fragments include tropoelastin not including one or more amino acids of a particular domain, or not including one or more domains.

F/L lacking 22 and 26A (SHELΔ26A) is the most common isoform expressed by humans in vivo. It corresponds to the Full Length sequence above, but lacks domains 22 and 26A. F/L lacking 22 but with 26A (SHEL) is an isoform corresponding to Full Length tropoelastin but lacking domain 22. SHELΔ26A and SHEL isoforms are referenced in Wu et al. (1999) *J. Biol. Chem.* 274, 21719-21724.

SHEL N-18 is a construct spanning from domain 2 (N-terminus) up to and including domain 18. SHEL17-27 is a construct spanning from domain 17 up to and including domain 27. SHEL 27-C is a construct spanning from domain 27 up to and including domain 36 (C-terminus). Clarke et al. (2005) Biochemistry. 44(30):10271-81 references these constructs.

D36 domain has the following amino acid sequence: IFPGACLGKACGRKRK (SEQ ID NO: 1). As used herein, reference to D36 includes portions of this sequence, and/or D36 in combination with other domain regions, and derivatives of domain 36 and its sub-fragments, covalently linked to a molecular extension containing at least one primary amine for the purpose of covalent attachment to provide a composite protoelastin material". The sequence of domain 36 and its importance to integrin binding is detailed in Rodgers and Weiss (2004) *Biochimie* 86, 173-178.

Protoelastin is recombinant human tropoelastin (and variations on this sequence), including alternative splicing constructs, fragments, and genetically engineered constructs which may include insertions or deletions based on the human elastin sequence, either cross-linked or uncrosslinked, which is engineered for use as a biomaterial by covalent binding, crosslinking, blending, laminating, or coating.

Thrombogenicity refers to the tendency of a material in contact with blood to produce a thrombus, or clot. All surfaces will be thrombogenic, given low enough flow rates and high enough viscosity, though some perform better than others. Existing vascular materials like stainless steel, Dacron and ePTFE are all considered to be pro-thrombogenic. Both collagen and fibronectin are also highly thrombogenic, while trials of the protoelastin described herein show it to be no more thrombogenic than saline.

Endothelialization refers to the attachment and proliferation of endothelial cells on the surface of the substrate material. The luminal surface of the vasculature is covered by a layer of endothelial cells, which mediate blood interactions and modulate the proliferation of other cell types like smooth muscle cells. The endothelial cell lining is easily damaged and this is known to occur during stent deployment, or bypass grafting of autologous vessels. This damage can lead to a host of negative performance consequences such as neointimal hyperplasia and clot formation. Currently available commercial synthetic vascular materials have no endothelial cells when implanted and rely on host cells attaching and proliferating. The literature generally indicates that the faster a functioning endothelial cell layer can be recruited, the better the vascular material will perform.

As described in U.S. Pat. No. 7,258,988, the vascular endothelium forms a "container" for blood. As long as this cellular layer remains intact and is functioning normally, a non-thrombogenic surface is presented to the circulating blood, allowing it to remain fluid and perform its nutritive functions unimpeded by intravascular clotting. Physical disruption of the endothelial lining, even on a microscopic scale, elicits an immediate hemostatic response, involving localized activation of the coagulation cascade and the adherence and aggregation of platelets, an adaptive reaction that serves to limit blood loss at sites of injury."

Mechanically stable refers to sufficient mechanical stability/strength to tolerate physiological blood flows (measured as ultimate tensile strength at present) and to withstand deformation and aneurysm formation. The uniqueness of the elastin-polymer constructs extends to compliance and elasticity, a characteristic lacking from commercial grafts and one attributed to their failure (as measured by Young's modulus at present). Mechanical stability includes long term biological stability, such that the material is not eroded significantly over time, and the ability to withstand deformation during surgical or percutaneous delivery and implantation such as by suturing or by high-pressure balloon inflation.

II. Materials

The materials disclosed herein include human recombinant tropoelastin in combination with other synthetic or natural biomaterials to impart the desired mechanical and biological properties. In some of the preferred embodiments, the elastin is blended with the polymer; in other embodiments, the elastin is formed into a laminate with films or layers of polymer. In other embodiments, elastin is used as a coating for existing implantable materials.

A. Elastin

Elastin is an extracellular matrix protein that is found within skin, lungs, bladder, elastic cartilage and arteries. Elastin is an insoluble polymer that is assembled extracellularly and is composed of monomer tropoelastin molecules. Elastin is principally synthesized during the development or growth of tissues, with tropoelastin expression occurring during mid- to late fetal or embryonic periods.

1. Tropoelastin

Figure 1B:
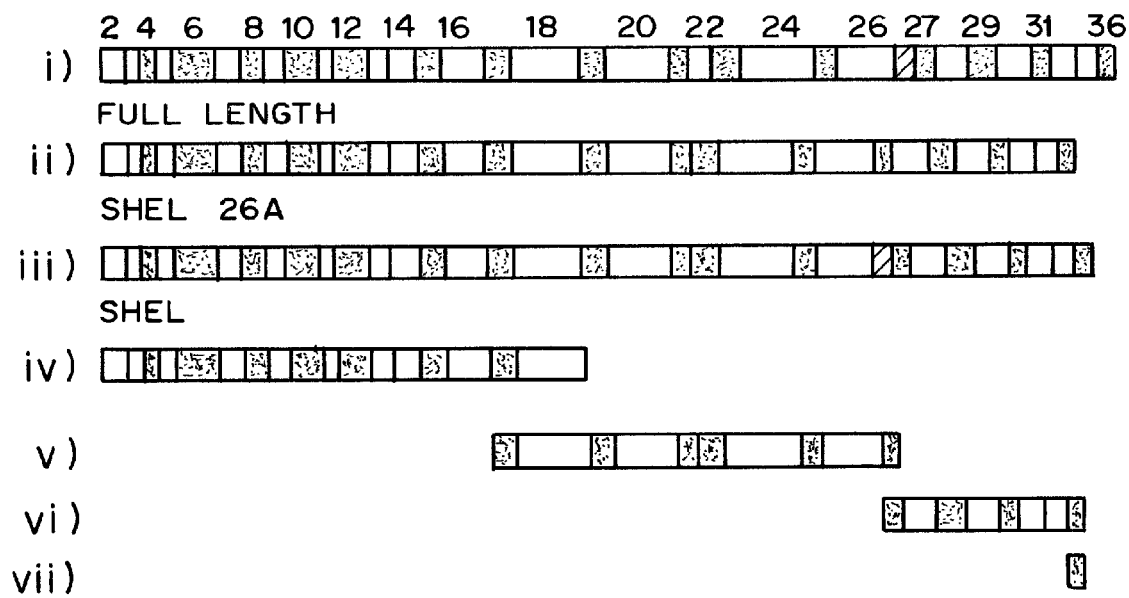
FIG. 1B is a schematic representation of common tropoelastin splice forms and derivatives. Hydrophilic exons are shaded, domain 26A is striped. (i) all possible domains expressed by the elastin gene; (ii) a common isoform, lacking domains 22 and 26A; (iii) a common isoform lacking domain 22, but including 26A; (iv) construct encompassing the N-terminus; (v) construct encompassing the center of elastin; (vi) construct encompassing the C-terminus; and (vii) construct encompassing domain 36.
Figure 1C:
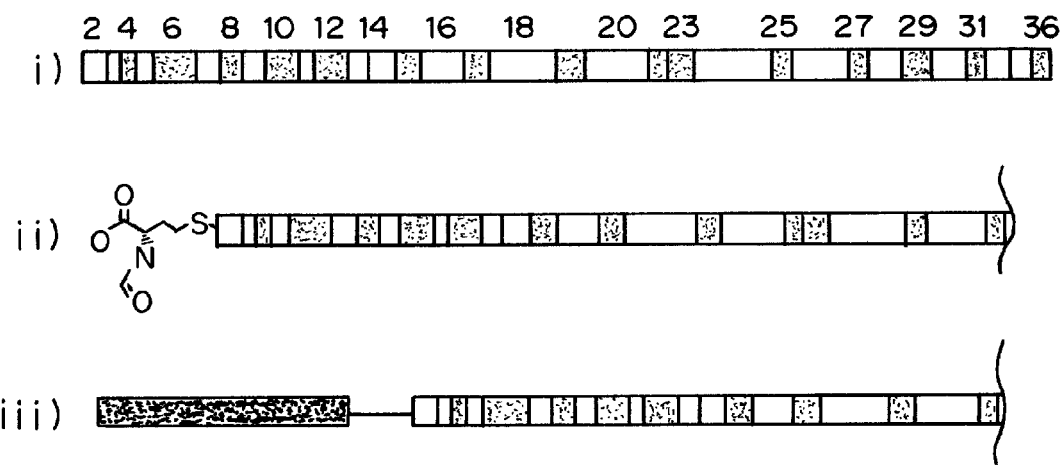
FIG. 1C is a schematic of possible modifications to recombinant tropoelastin. (i) a frequently expressed isoform; (ii) formyl methionine modification of the N-terminus; and (iii) N-terminal tag (short peptide as his-tag) modification.

Tropoelastin is encoded by a single-copy gene including 36 domains, as shown in FIG. 1A. Domain 1 is a signal peptide. Domains 2, 3, 5, 7, 9, 11, 13, 14, 16, 18, 20, 22, 24, 26, 28, 30, 32 and 33 are hydrophobic domains; domains 4, 6, 8, 10, 12, 15, 17, 19, 21, 23, 25, 27, 29, and 31 are hydrophilic crosslinking exons; domain 26A is a hydrophilic exon; domain 36 is the hydrophilic C-terminus. Domains 26A and 36 are not easily characterized. Exons 22, 23, 24, 26A, 32 and 33 are subject to alternative splicing, giving rise to multiple tropoelastin isoforms. Alternative splicing of tropoelastin mRNA transcripts results in various tropoelastin isoforms. Representative tropoelastin splice forms and derivatives are shown in FIG. 1B. (i) is the tropoelastin including all possible domains expressed by the elastin gene; (ii) is a common isoform lacking domains 22 and 26A; (iii) is a common isoform lacking domain 22, but including 26A; (iv) is a construct encompassing the N-terminus; (v) is a construct encompassing the center; (vi) is a construct encompassing the C-terminus; and (vii) is a construct encompassing domain 36. FIG. 1C is a schematic of common derivatives of tropoelastin: (i) a frequently expressed isoform; (ii) formyl methionine modification of the N-terminus; and (iii) N-terminal tag such as His-tag.

Human tropoelastin is synthesized as an approximately 72,000 Da protein by a variety of cells including smooth muscle cells, endothelial cells, fibroblasts and chondrocytes. Secretion is followed by an orchestrated interplay of macromolecular partners that assist in delivering tropoelastin monomers to sites of elastogenesis. Such interactions facilitate identification of sites for elastin assembly through associating microfibrillar proteins and encourage deposition with previously accreted tropoelastin. Tropoelastin is encoded by a single gene that possesses 36 exons and gives rise to multiple isoforms. In human tropoelastin the mRNA encodes a 72,000 Da polypeptide which undergoes splicing and removal of signal peptide, leaving a mature protein with a molecular weight ranging from 60,000 Da to 70,000 Da (Visconti et al., 2003) (Visconti et al., (2003) *Matrix Biol,* 22, 109-21). Domains 22, 23, 24, 26A, 30, 32 and 33 undergo developmentally regulated alternative splicing (Bashir et al., 1989) (Bashir et al., (1989) *J Biol Chem,* 264, 8887-91), resulting in these multiple isoforms (Parks and Deak, 1990) (Parks and Deak, (1990) *Am J Respir Cell Mol Biol,* 2, 399-406). One skilled in the art will appreciate that these isoforms behave similarly for the purposes of their use as a biomaterial. These can be modified by substituting, adding, or deleting one or more amino acids within these domains, or one or more domains.

Preferred tropoelastin splice variants include fragments encompassing roughly the first third of the molecule (called N18), the middle third (called 17-27) and the C-terminal third (called 27-C). This also extends to individual domains and short peptides suspected to be important to cell recognition, such as domain 36.

Domain 36, the C-terminus of tropoelastin, is known to be highly conserved (greater than 78%) across species and contains two characteristic features which may impart some conformational preference. Two cysteine residues are found in domain 36 and form a disulfide bond, while the protein terminates with the positively charged RKRK (SEQ ID NO: 2) sequence. Integrin binding in this region (Rodgers and Weiss, 2004) (Rodgers and Weiss, (2004) *Biochimie,* 86, 173-178) and evidence of interaction with glycosaminoglycans that mediate cell adhesion (Broekelmann et al., 2005) (Broekelmann et al., (2005) *J Biol Chem.* 280(49):40939-47) are further indications of the importance of the conserved C-terminus.

2. Conversion of Tropoelastin to Elastin

Elastin is an extremely durable and insoluble biopolymer and is formed through the lysine-mediated cross-linking of its soluble precursor tropoelastin. In vivo, tropoelastin is excreted into the extracellular space and is quickly cross-linked by the action of an enzyme called lysyl oxidase. Complex, permanent covalent cross-links are formed. Conversion to elastin occurs in vivo by the action of lysyl oxidase, which converts the epsilon amine on side chains of occasional lysines in tropoelastin to the adipic semi-aldehyde. Coacervation juxtaposes modified and unmodified lysines to facilitate irreversible covalent cross-linking. Tropoelastin and Elastin are used interchangeably herein after crosslinking.

3. Purification of Elastin

Historically, elastin and tropoelastin have been difficult to isolate. Both can be harvested from a variety of animal sources including bovine, porcine and equine, preferably from elastin rich tissue such as ligament and aorta. Elastin is extracted from these tissue using harsh conditions including refluxing in ethanol, autoclaving, acid and trypsin digestion and sodium hydroxide. These conditions strip away fats and other matrix proteins like collagen, but also damage the elastin.

Obtaining the protein monomer precursor of elastin (tropoelastin) in large quantities remains difficult, with the monomer cross-linked into elastin before it can be harvested. Initially, isolation relied on animal hosts, usually pigs, with a copper deficient diet (Mecham and Foster, (1979) *Biochimica et Biophysica Acta,* 577, 147-58), deactivating the enzymes cross-linking function and perturbing elastic fiber assembly. The time and effort involved in this procedure was certainly not reflected in the average yield of 0.1% tropoelastin to aortic weight (Sandberg and Wolt, (1982) *Methods in Enzymology,* 82 Pt A, 657-65). The method evolved marginally to introduce an enzyme inhibitor (Rich and Foster, (1984) *Biochem J.* 217, 581-4) and chicks (Abraham and Carnes, (1978) *J Biol Chem,* 253, 7993-5), but remained inefficient.

As an alternative to tropoelastin, some researchers artificially make 'soluble elastin' by chemically treating elastin samples. Both α-elastin (Cox et al., (1973) *Biochim Biophys Acta,* 317, 209-13), an oxalic acid derivative of elastin, and κ-elastin, solubilized with potassium hydroxide have been investigated. Investigations with these systems continue to the present, while it is recognized that chemically degraded elastin cannot precisely represent the in vivo monomer (Starcher et al., (1973) *Biochim Biophys Acta,* 310, 481-6). 'Soluble elastin' the soluble product of acid or base digestion of animal derived elastin is commercially available and the most commonly used variant in the literature.

4. Recombinant Tropoelastin

Recombinant tropoelastin was first expressed as a fusion protein in an *E. coli* bacterial system some 17 years ago (Indik et al., (1990) *Arch Biochem Biophys,* 280, 80-6). The HPLC purified protein exhibited an amino acid composition and size (72 kDa) anticipated for the full length clone used. The high purity of the recombinant protein produced in this system was beneficial, while persistent smaller fragments and the limitation of small yields were problematic, with only 2-4 mg produced per liter of culture. Soon after, a recombinant 60 kDa mature form of tropoelastin (Martin et al., (1995) *Gene,* 154, 159-66) was expressed, following significant improvements to the bacterial expression system. This system boasts significantly higher yields of protein. Tropoelastin is now produced in gram quantities in a highly reproducible manner. Other groups have been involved in recombinant tropoelastin production, but none can produce it in comparable high yields and high purity.

This recombinant protein is recognized by cells to form elastin (Stone et al., (2001) *Amer. J. Respir. Cell. Mol. Biol.* 24, 733-739), associates at 37° C. (Toonkool et al., (2001) *J. Biol. Chem.* 276, 28042-50) and can be cross-linked chemically to form an elastin-like material (Mithieux et al., (2004) *Adv. In Protein Chemistry,* 70, 437-61). While this system can produce large quantities of high purity protein, monomer can be expressed in other recombinant systems or chemically synthesized.

Recombinant human elastin behaves very differently from elastin sourced from animals, the most common type discussed in the prior art. Biocompatibility and elasticity are intrinsic properties of endogenous elastin as demonstrated by its crucial role in aortic function. It mediates interactions with endothelial cells and provides recoil and, in combination with collagen, strength. Recombinant tropoelastin is preferably expressed in the *E. coli* expression system described in U.S. Pat. No. 6,232,458. U.S. Pat. No. 6,232,458 is directed to a method of recombinantly producing large scale quantities of human tropoelastin in a bacterial system.

5. Chemically Modified or Derivatized Tropoelastin

The tropoelastin can be chemically modified in a variety of ways known in the art. The tropoelastin can be modified at the N-terminus, the C-terminus, and/or at one or more of the sidechains of the amino acids of tropoelastin. Suitable chemical modifications include, but are not limited to, pegylation, formylation, acylation, attachment of linkers, such as peptide linkers, attachment of growth factors and/or cell attachment moieties, alkylation, and combinations thereof. Exemplary chemical modifications include, but are not limited to, acylation of the N-terminus, formylation of the N-terminus, N-terminal extensions, amidation of the C-terminus, glycosylation, iodination of tyrosine, and alkylation reactions, such as methylation.

6. Protoelastin

Protoelastin, as used herein, is a material that incorporates tropoelastin. The material is engineered to have desirable properties for a particular use. For example, the protoelastin may be engineered for human clinical vascular applications. In this embodiment, the preferred material for use as a vascular graft has an ultimate tensile strength of at least 3 MPa.

Typically, increased strength is obtained through the selection of the other components of the composition and chemical modification, such as cross-linking of the recombinant human tropoelastin. Protoelastin, in the preferred embodiment, displays physical and structural properties similar to those of naturally occurring elastin including similar compliance and favorable cellular interactions (Mithieux and Weiss, (2005) *Adv. Protein Chem.* 70, 437-61). These properties also can be manipulated by changing protein concentration, cross-linker type and polymerization conditions to engineer a material to suit a range of vascular biomaterial applications.

B. Polymeric Materials, Substrates and Laminates

The tropoelastin is applied to, crosslinked with, tethered to, blended with, or laminated as part of, one or more materials to form a protoelastin material.

1. Films, Coatings and Laminates

The tropoelastin can be applied to ceramic, bone, metal, or polymer substrates to provide a biocompatible elastic surface. Typical metals include stainless steel and titanium. In one embodiment, the material is or includes one or more biodegradable or non-biodegradable synthetic polymers such as polylactides, polyglycolic acids, polycaprolactones, polycaprolactams, polyhexamethylene adipamide, polycarbonates, polyamides, polyanhydrides, polyamino acids, polyesters, polyacetals, polycyanoacrylates, polyvinyl alcohols, polyvinyl chlorides, polyethylenes, polyurethanes, polypropylenes, polyacrylates, polystyrenes, polyvinyl oxides, polyvinyl fluorides, poly(vinyl imidazoles), polyethylene oxides, polytetrafluoroethylenes, silicone polymers and copolymers and combinations thereof. In another embodiment, the material is or includes one or more natural materials such as a protein, sugar or polysaccharide, or combination thereof. Representative examples include collagen, preferably type 1 and/or type 3, fibrin, gelatin, vitronectin, fibronectin, laminin, hyaluronic acid, glycosaminoglycans, their derivatives and mixtures thereof. Preferred glycosaminoglycans include chondroitin sulfate, dermatan sulfate, keratan sulfate, heparan sulfate, heparin and hyaluronan.

In the preferred embodiment, the graft is formed from a synthetic non-biodegradable polymer such as polyethylene terephthalate (DACRON®), expanded polytetrafluoroethylene (ePTFE) and polyurethanes. Examples of suitable commercially available materials include PELLETHANE®, CHRONOFLEX®, ESTANE®, ELAST-EON®, TEXIN®, DEMOSPAN®, CORETHANE®, TECHNOFLEX®, TECHNOTHANE®, BIORUBBER® and BIOSPAM®.

As demonstrated in the examples, it is critical to tether or crosslink the tropoelastin to the substrate, thereby forming a protoelastin material. Tethering is required to avoid the elastin from being removed by the shear forces associated with the passage of blood through the blood vessel and graft.

As used herein, a film or coating will typically be in the range of a few microns in thickness, or less. In a preferred embodiment, the coating consists primarily of protoelastin that promotes endothelial cell growth on a surface.

Figure 2:
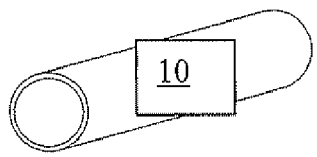
FIG. 2 is a prospective view of a protoelastin only tube.

FIGS. 3-5 exemplify some of the protoelastin biomaterials. FIG. 2 is a schematic of a tube 10 formed of protoelastin. A tube formed solely of tropoelastin, even cross-linked tropoelastin, does not have the mechanical properties necessary for use in vascular applications.

Figures 3A, 3B:
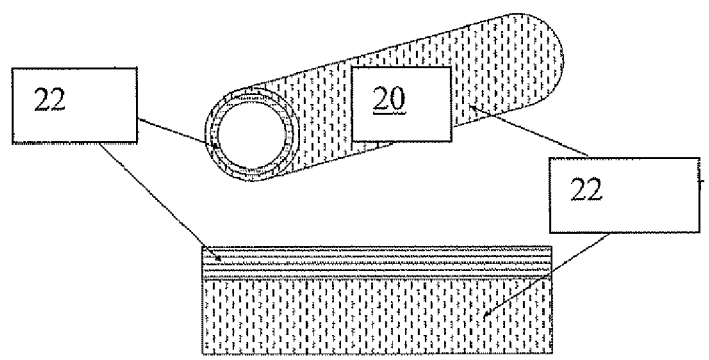
FIGS. 3A and 3B are a prospective view of a tube (FIG. 3A) and a cross-sectional view (FIG. 3B) of a copolymer luminally coated with protoelastin.

In a preferred embodiment as described herein, shown in FIGS. 3A and 3B, tube 20 is a polymeric graft 22 having a crosslinked elastin layer 24 tethered on the inside luminal surface.

Figures 4A, 4B:
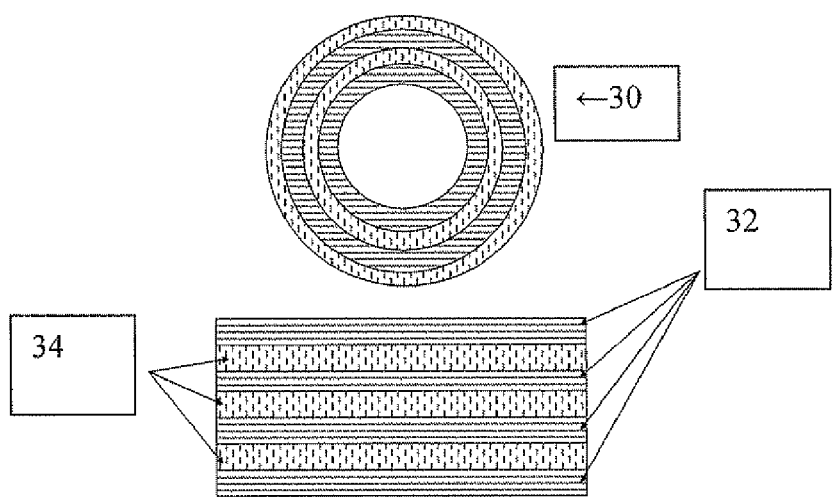
FIGS. 4A and 4B are a prospective view of a tube (FIG. 4A) and a cross-sectional view (FIG. 4B) of a protoelastin-copolymer laminate, with the protoelastin on the luminal surface.
Figures 5A, 5B:
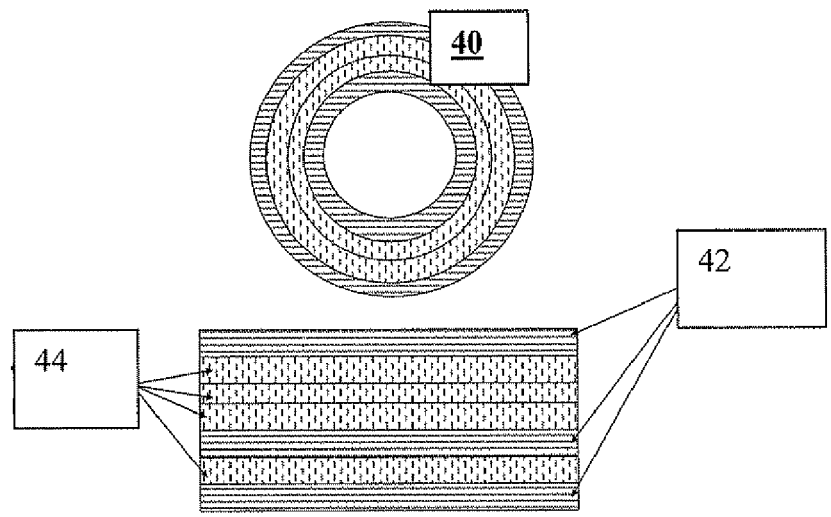
FIGS. 5A and 5B are a prospective view of a tube (FIG. 5A) and a cross-sectional view (FIG. 5A) of a non-alternating copolymer laminate, with the protoelastin on the luminal surface.
Figure 6:
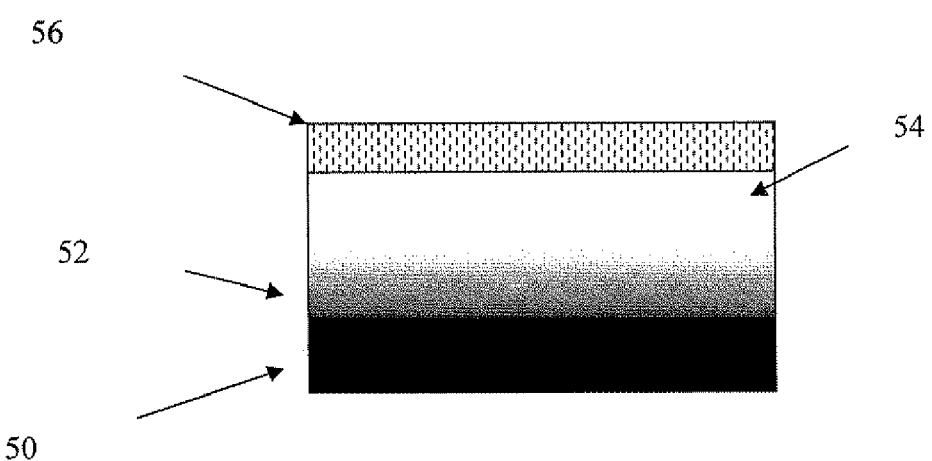
FIG. 6 is a schematic of a metallic substrate with a graded transition to an activated upper polymer layer, such as embedded acetylene, hexane or other carbon-containing chemical, using standard technologies. This upper layer is activated by PIII or plasma treatment to facilitate protein attachment. Protoelastin is obtained by covalent attachment of protein to this upper layer by immersion in a solution of tropoelastin or tropoelastin derivatives.

FIGS. 4A and 4B are schematics of tube 30 formed of layers of tropoelastin 34 alternating with a layer of polymer 32. FIGS. 5A and 5B are schematics of tube 40 formed of layers of tropoelastin 44 alternating with one or more layers of polymer 42. FIG. 6 is a schematic of metallic substrate 50 with a graded transition 52 to an activated upper polymer layer 54 (such as embedded acetylene, hexane or other carbon-containing chemical) using standard technologies. This upper layer 54 is activated by PIII or plasma treatment to facilitate protein attachment. Protoelastin 56 is obtained by covalent attachment of protein to this upper layer by immersion in a solution of tropoelastin or tropoelastin derivatives.

2. Polymeric Blends

The material properties of the protoelastin can be modified by blending the tropoelastin with one or more other polymeric materials. The properties can be further modified through crosslinking and/or covalent coupling.

In one embodiment, the material is or includes one or more biodegradable or non-biodegradable synthetic polymers such as polylactides, polyglycolic acids, polycaprolactones, polycaprolactams, polyhexamethylene adipamide, polycarbonates, polyamides, polyanhydrides, polyamino acids, polyesters, polyacetals, polycyanoacrylates, polyvinyl alcohols, polyvinyl chlorides, polyethylenes, polyurethanes, polypropylenes, polyacrylates, polystyrenes, polyvinyl oxides, polyvinyl fluorides, poly(vinyl imidazoles), polyethylene oxides, polytetrafluoroethylenes, silicone polymers and copolymers and combinations thereof. The protoelastin can include more than one polymer component.

In another embodiment, the material is or includes one or more natural materials such as a protein, sugar or polysaccharide, or combination thereof. Representative examples include collagen, preferably type 1 and/or type 3, fibrin, gelatin, vitronectin, fibronectin, laminin, hyaluronic acid, glycosaminoglycans, their derivatives and mixtures thereof. Preferred glycosaminoglycans include chondroitin sulfate, dermatan sulfate, keratan sulfate, heparan sulfate, heparin and hyaluronan.

C. Additional Materials

The protoelastin materials can be used for drug delivery, incorporating a therapeutic, prophylactic or diagnostic agent, or incorporate materials such as growth factors which facilitate attachment and proliferation of one or more cell types.

Preferred therapeutic agents which may be delivered include: Growth Factors: vascular endothelial growth factor, fibroblast growth factor, hepatocyte growth factor, connective tissue growth factor, placenta-derived growth factor, angiopoietin-1 and granulocyte-macrophage colony-stimulating factor.

Agents modulating cellular behavior in relation to bioprosthesis: microfibrillar collagen, fibronectin, fibrin gels, synthetic Arg-Gly-Asp (RGD) adhesion peptides, tenascin-C, Del-1, CCN family (e.g. Cyr61) hypoxia-inducible factor-1, acetyl choline receptor agonists and monocyte chemoattractant proteins.

Gene delivery agents: viral vectors for gene delivery (adenoviruses, retroviruses, lentiviruses, adeno-associated viruses) and non-viral gene delivery agents/methods (e.g. polycation polyethylene imine, functional polycations consisting of cationic polymers with cyclodextrin rings or DNA within crosslinked hydrogel microparticles, etc.).

Agents modulating cell replication/proliferation: target of rapamycin (TOR) inhibitors (including sirolimus, everolimus and ABT-578), paclitaxel and antineoplastic agents (including alkylating agents, e.g. cyclophosphamide, mechlorethamine, chlorambucil, melphalan, carmustine, lomustine, ifosfamide, procarbazine, dacarbazine, temozolomide, altretamine, cisplatin, carboplatin and oxaliplatin), antitumor antibiotics (bleomycin, actinomycin D, mithramycin, mitomycin C, etoposide, teniposide, amsacrine, topotecan, irinotecan, doxorubicin, daunorubicin, idarubicin, epirubicin, mitoxantrone and mitoxantrone), antimetabolites (deoxycoformycin, 6-mercaptopurine, 6-thioguanine, azathioprine, 2-chlorodeoxyadenosine, hydroxyurea, methotrexate, 5-fluorouracil, capecitabine, cytosine arabinoside, azacytidine, gemcitabine, fludarabine phosphate and aspariginase), antimitotic agents (vincristine, vinblastine, vinorelbine, docetaxel, estramustine) and molecularly targeted agents (imatinib, tretinoin, bexarotene, bevacizumab, gemtuzumab ogomicin and denileukin diftitox))

Steroids: Corticosteroids, estrogens, androgens, progestogens and adrenal androgens Antiplatelet, antithrombotic and fibrinolytic agents agents: glycoprotein IIb/IIIa inhibitors, direct thrombin inhibitors, heparins, low molecular weight heparins, platelet adenosine diphosphate (ADP) receptor inhibitors, fibrinolytic agents (streptokinase, urokinase, recombinant tissue plasminogen activator, reteplase and tenecteplase etc).

Gene targeting molecules: small interference (si) RNA, micro RNAs, DNAzymes and antisense oliogonucleotides Cells: progenitor cells (endothelial progenitor cells, CD34+ or CD133+ monocytes, hemopoietic stem cells, mesenchymal stem cells, embryonic stem cells) and differentiated cells (endothelial cells, fibroblasts and smooth muscle cells)

Drug delivery agents: mucoadhesive polymers (e.g. thiolated polymers)

Pharmacologic agents of local treatment of atherosclerosis: high density lipoprotein cholesterol (HDL), HDL mimetics and hydroxymethylglutaryl CoA (HMG-CoA) reductase inhibitors.

III. Methods of Manufacture of Materials and Devices

A. Biomedical Devices and Applications

The manufacture of the tropoelastin and protoelastin is discussed above.

These materials are then applied to or formed into material which forms, in whole or in part, a material for biomedical use. The application will determine the selection and design of the mechanical properties. The material can be applied as a part of a variety of clinical vascular applications including a vascular conduit, a stent, a stent-graft, a surgically or percutaneously implantable heart valve, a vascular/septal occlusion device, a vascular closure device or as a surface coating for a vascular device/application. Other useful materials are matrices for tissue engineering, bone implants and prosthetics including pins, rivets, screws and rods, as well as artificial knees and other joints, especially at the surfaces where the metal ceramic or bone interfaces with the host tissue. Still other application include the use of the material for delivery of therapeutic, prophylactic or diagnostic agents, as discussed above. In still other applications, the materials are used for non-therapeutic applications, for example, in cell culture.

1. Vascular Grafts

Elastin is one of the major structural components of vessels and conduits. It makes up 28-32% of large arteries and imparts recoil and durability to these conduits. Elastin is formed through the cross-linking of its soluble precursor tropoelastin, which is initiated through the action of the enzyme lysyl oxidase (LOX) (Kagan and Sullivan, (1982) *Methods in Enzymology,* 82, 637-650) on exposed lysines of tropoelastin. Importantly, elastin is responsible for the two vessel characteristics that are deficient in current graft materials and are implicated in their failure: compliance and favorable cellular interaction. In the artery for example, elastin is found in distinct locations performing different functions. The adventitia is characterized by elastin fibers which are interspersed with collagen, providing mechanical strength and recoil, emphasized by the decreased arterial compliance and hypertension observed in mice with a single deletion in the elastin gene ((Wagenseil et al., (2005) *Amer. J. Physiol.—Heart and Circulation Physiology,* 289, H1209-17). A continuous sheet of elastin also forms the internal elastic lamina, providing a surface on which endothelial cells form a monolayer and a covering for the layer of smooth muscle cells that make up the tunica media. The total absence of elastin, again in a mouse model, results in the early death of the animals from uncontrolled proliferation of smooth muscle cells causing arterial obstruction (Li et al., 1998).

In the preferred embodiment, the combination of tropoelastin and a copolymer that is engineered for human clinical vascular applications has an ultimate tensile strength of at least 3 MPa. Each component can be either a homogenous material or a composite of two or more materials. The components may be arranged in alternating or non-alternating patterns. The protoelastin is present in an effective amount and location to promote vascular compatibility, including increased endothelialization, and/or reduced thrombogenicity, and/or reduced neointimal hyperplasia.

2. Implants and Prosthetics

Other useful materials are matrices for tissue engineering and/or drug delivery, bone implants and prosthetics including pins, rivets, screws and rods, as well as artificial knees and other joints, especially at the surfaces where the metal, ceramic or bone interfaces with the host tissue. In the majority of these cases, the critical role of the protoelastin is to increase the biocompatibility of the implant or matrix, promoting cell attachment or diminishing the formation of scar tissue, abnormal proliferation of cells (i.e., restenosis or scarring), and integration of the implant into the host.

3. Tissue Culture

The protoelastin can be applied to the surface of a tissue culture container. The tissue culture container can be a flask, a dish, a multi-well plate, a micro plate or a slide. The coating should be effective to promote cell attachment and cell proliferation, preferably promoting the formation of a confluent cellular surface coating.

B. Design and Modification of Mechanical Properties

For use as a biomaterial, elastin's primary properties have traditionally been seen as elasticity and resilience to degradation by proteases. Throughout the literature it has long been acknowledged that elastin alone lacks sufficient mechanical strength to be used as a stand alone biomaterial, especially in the vascular space. A major limitation of elastin as a vascular graft material is its low ultimate tensile strength.

Required mechanical stability for a predominantly elastin biomaterial will vary dependant on the application. If it is used as a coating for an ePTFE graft, the tensile strength can effectively be zero and the measure of its success will be its persistence to on the surface. An elastin based conduit or graft will have the highest requirements, with a necessity to at least match in vivo examples (human aorta having a tensile strength of 1 to 2 MPa and a stiffness of 10 to 12 MPa).

Mechanical strength is achieved through 1) control of formulation and 2) control of fabrication. In terms of formulation one can manipulate the tropoelastin concentration, the type (and duration) of cross-linking and the intermingling of other copolymers in solution. Strength is also a function of the fabrication technique.

The mechanical properties of the protoelastin can be modified by changing the protein concentration (this can mean thickness, but also includes actual percentage of protein in solution. By way of example, when electrospinning the concentration of tropoelastin in solution can be raised from 10% w/v to 20% w/v—or the original solution can be delivered for a longer time, giving a thicker material. Currently it is common to electrospin tropoelastin solutions ranging from 1% w/v up to 25% w/v—depending on the type and proportion of copolymer. The listed example of a solution containing 5% w/v tropoelastin and 5% w/v polycaprolactone is representative of a typical blend. We would prefer not to be limited to a range, given that the amount of protein needed for coating of a surface could well be much less and the blend ratios of some polymers have not yet been elucidated) the cross-linking type and duration, the presence and type of copolymer, and the fabrication method. In this context fabrication method refers to the method of producing the protoelastin material. Specifically electrospinning is currently preferred though centrifugally cast molding is also listed in the examples. Electrospinning will generally speaking result in a more robust end product than casting, which in turn gives a stronger material than one molded under gravity alone.

1. Crosslinking of Elastin

The protoelastin can be an enzymatically or chemically cross-linked to itself, to one or more other polymers or to a substrate. Enzymatic cross-linking can be achieved using any lysyl oxidase capable of converting epsilon amines to adipic semi-aldehydes or through the enzyme catalysis of transglutaminase. The chemical cross-linking can be achieved using any from the group of reagents with at least one amine reactive group, for example, using a chemical cross-linking reagent such as bis(sulfosuccinimidyl)suberate (BS3), 1-Ethyl-3-[3-dimethylaminopropyl]carbodiimide Hydrochloride) (EDC), glutaraldehyde, N-hydroxysuccinimide) (NHS) and 1,6-diisocyanatohexane (HMDI) and combinations thereof.

2. Methods of Making Coatings and Covalent Coupling to a Substrate

The tropoelastin can be applied to a surface by spraying, dipping, or other methods known to those skilled in the art.

In one embodiment the substrate material is modified to create reactive surface groups which facilitate covalent interaction. In the case of inert polymeric materials like ePTFE, the surface requires activation. Both 'classical' plasma processes (Bilek et al. (2004) In *Smart Materials III*, Vol. 5648 (Ed, Wilson, A. R.) SPIE, pp. 62-67.) and higher energy plasma immersion ion implantation (Bilek et al. (2002) *Surface and Coatings Technology*, 156, 136-142.) (PIII) are applicable. In a preferred embodiment, the tropoelastin is covalently tethered to the polymer when a solution of the protein is incubated with the activated surface. PIII has recently been shown to increase the functional lifetime of attached proteins and may be preferred (Nosworthy et al. (2007) *Acta Biomater*, 3, 695-704.). Similarly, Dacron® surfaces can be predisposed to covalent attachment of tropoelastin using chemical means (Phaneuf et al (1995) *Journal of Applied Biomaterials*, 6, 289-99.).

Metallic substrates can be also be functionalized by applying the PIII process to the substrate while it is immersed in a carbon containing plasma or in a vapour of the monomer used to deposit the plasma polymer layer or by codeposition of a graded substrate/polymer layer which terminates in the polymer. In a preferred embodiment this technique would be used to bind tropoelastin to a range of metals including stainless steel.

3. Methods of Making Laminates

The protoelastin can be in the form of a laminate, wherein the tropoelastin is layered onto one or more layers of polymer, preferably stabilized by cross-linking and/or covalent tethering to the substrate, which may then be covered with one or more additional layers of polymer. For vascular applications and implants that interface with cells or tissue, the luminal side of the laminate or exterior portion of the implant is preferable covered with the protoelastin. The selection of the polymer(s), the number and thickness of the polymer and tropoelastin layers, and the degree of cross-linking of the tropoelastin will determine the strength and rigidity of the laminate.

4. Methods of Making Polymer Blends

The tropoelastin can be blended with one or more polymers, as described above, to create materials having desired mechanical properties. The properties will depend on the polymer that is selected, the relative concentration of polymer to tropoelastin, and the method of blending and cross-linking or covalent coupling, if any.

The polymeric materials can be blended with the tropoelastin dissolved in an appropriate mutual solvent. For electrospinning, materials are best dissolved in polar organic solvents. 1,1,1,3,3,3-hexafluoropropanol (HFP) is preferred. Other solvents such as tetrahydrofuran (THF), N,N-dimethylformamide (DMF), trifluoroacetic acid (TFA) and dichloromethane can also be used. Tropoelastin blends can also be prepared in aqueous systems like phosphate buffered saline (PBS) for other fabrication techniques by taking advantage of its unique temperature behaviors (e.g. increased solubility at 4° C.).

5. Electrospinning of Fibers

Electrospinning of fine fibers provides the greatest control over the architecture of the constructs. By way of example, electrospun recombinant human tropoelastin has a tensile strength of about 0.5 MPa, but when it is co-spun with collagen in a 50:50 ratio, strength is doubled. When tropoelastin is electrospun with a polymer such as polycaprolactone, the strength of the final material is even greater (up to 3 MPa), while the elasticity contribution of elastin can be retained. Biostable polymers such as nylon and Dacron are preferred.

Composite tubular materials that have favorable characteristics for grafting have been engineered using the electrospinning technique. The tubes are suturable, porous (when viewed by scanning electron microscopy) and can be reproducibly manufactured. In a preferred embodiment, the tubes are composites of tropoelastin and polycaprolactone, subsequently cross-linked with HMDI. Non-degradable or less degradable polymers that are used with the tropoelastin will be more stable.

The material can be applied as a part of a variety of clinical vascular applications including a vascular conduit, a stent, a stent-graft, a surgically or percutaneously implantable heart valve, a vascular/septal occlusion device, a vascular closure device or as a surface coating for a vascular device/application.

The present invention will be further understood by reference to the following non-limiting examples.

EXAMPLE 1

Protoelastin Synthesis Using Chemical Cross-Linking of Tropoelastin

Tropoelastin was dissolved in cold phosphate buffered saline (PBS) at a concentration of 100 mg/ml. The amine reactive cross-linker, bis(sulfosuccinimidyl)suberate (BS3) was freshly prepared by dissolving in PBS immediately prior to use to a concentration of 100 mM. The solutions were mixed in a 1:10 ratio to give a final cross-linker concentration of 10 mM. The solution was poured into a mould, prior to placement at 37° C. to facilitate coacervation and cross-linking. The resulting protoelastin was washed repeatedly with PBS and stored in a sterile environment.

EXAMPLE 2

Protoelastin Synthesis Using HMDI 100 mg of tropoelastin was placed in a small weight boat. In 10 µl aliquots, 100 µl of PBS was added to the tropoelastin slowly over several minutes. With the addition of each aliquot, a spatula was used to fold the solution into the protein. The tropoelastin eventually took on a gum-like consistency, which could be drawn into fibers and molded into shapes. To fix, the protein was submerged in a 10% 1,6-diisocyanatohexane (HMDI) in propanol solution and allowed to stand overnight. Elasticity was restored to the protoelastin by repeated washing in water and then in PBS.

EXAMPLE 3

Protoelastin Tube by Centrifugation

Tropoelastin (300 mg) was dissolved in cold PBS (2.7 ml) over several hours. When the protein solution had fully dissolved, BS3 (17.1 mg) was dissolved in a separate solution of PBS (300 μl). The tropoelastin and BS3 solutions were briefly mixed in an iced vessel, before being transferred to a suitable mould, also on ice.

The capped mould was placed in a centrifuge, preheated to 37° C. The mould was centrifuged at 1500 rpm for 5 min, before transfer to a 37° C. incubator where it was left to set overnight. After careful removal from the mold, the protoelastin tube was washed repeatedly with PBS and stored in a sterile environment.

EXAMPLE 4

Protoelastin Materials Prepared by Electrospinning

The electrospinning method was adapted from (Li et al., (2005) *Small*. 1(1):83-6). Briefly, a tropoelastin solution (5% w/v) was mixed with a copolymer (5% w/v) in 1,1,1,3,3,3-hexafluoropropanol. The homogenous solution was loaded into a 1 ml plastic syringe equipped with a blunt 18 gauge needle. Constant flow rates (0.5 ml/h) were achieved using a syringe pump (SP100 IZ Syringe Pump, Protech International) and the needle connected to the positive output of a high voltage power supply (ES30P/20W, Gamma High Voltage Research Inc.). The metallic target for the fibers carried a negative charge, provided by a second power supply. Electrospinning was carried out with the needle voltage set at 20 kV, the target voltage set at −3 kV and with an air gap distance of approximately 15 cm. Electrospun fibers were cross-linked using a 10% HMDI solution in isopropanol and washed with water and PBS.

EXAMPLE 5

Protoelastin Tubes by Electrospinning

To produce tubes by electrospinning requires the adaptation of standard procedures. A recent review details the broad variation in equipment set up design (Teo and Ramakrishna (2006) *Nanotechnology*, 17, R89-R106) Specifically, protoelastin based tubes were electrospun using a modified version of method employing knife-edge electrodes (Teo, et al. (2005) *Nanotechnology*, 16, 918-924.). Briefly, protein and polymer components were mixed in 1,1,1,3,3,3-hexafluoropropanol. The homogenous solution was loaded into a 1 ml plastic syringe equipped with a blunt 18 gauge needle. Constant flow rates (0.5 ml/h) were achieved using a syringe pump (SP100 IZ Syringe Pump, Protech International) and the needle connected to the positive output of a high voltage power supply (ES30P/20W, Gamma High Voltage Research Inc.). Fibers were drawn towards a carbon steel surgical blade (size 20), positioned approximately 15 cm from the needle tip. Fibers were collected on a rotating mandril which also oscillated longitudinally. Multiple layers, containing varied components could be built up in this fashion. The completed tube was rinsed in isopropanol, removed from the mandril and cross-linked overnight using a 10% HMDI solution in isopropanol. Finally, the tube was washed repeatedly with PBS and stored in a sterile environment.

EXAMPLE 6

Kaolin Clotting Assay Demonstrating Biocompatibility

Materials and Methods

The thrombogenicity of protoelastin was assessed in vitro, using an activated partial thromboplastin time (APTT) assay (Cullberg et al., (2001) *Brit. J. Cli. Pharmacol.*, 51, 71-91). This assay determines the ability of a material to effect the activation of the contact factors of coagulation and thus change the clotting time of human plasma.

Normal citrated plasma was mixed with a kaolin-phospholipid suspension (5 g/l in PBS) and left at 37° C. for 10 min, with occasional shaking. At exactly 10 min, pre-warmed $CaCl_2$ (0.025M) was added and a stopwatch started. The time for the mixture to clot was recorded. The protocol was repeated for plasma containing saline or ground protoelastin particles instead of kaolin, and again clotting times were recorded.

Results

Figure 7:
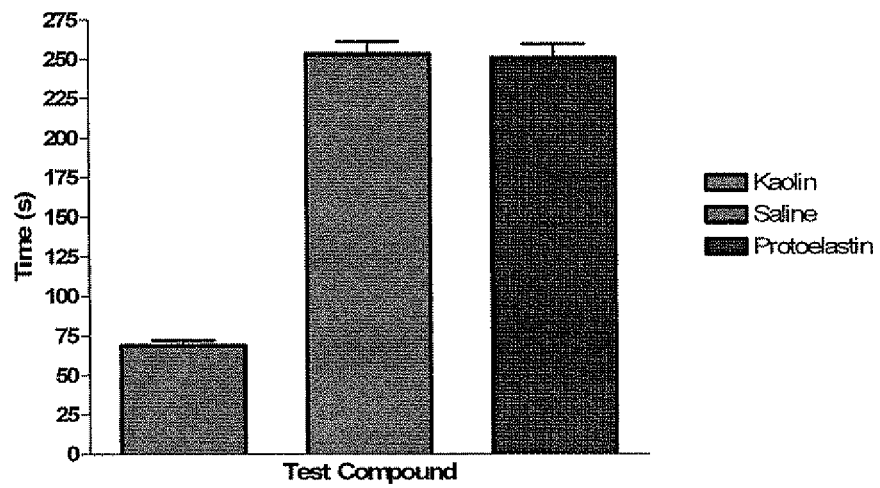
FIG. 7 is a graph of the clotting time (in seconds) for human plasma treated with kaolin (positive control), saline (negative control), and protoelastin, showing the clotting times for the saline and protoelastin are not significantly different.

Results are shown in FIG. 7 and demonstrate the non-thrombogenicity of the elastin coated material.

EXAMPLE 7

Attachment of Endothelial Cells to Protoelastin

Materials and Method

The effect of protoelastin, fibronectin and bovine serum albumin (BSA), on human umbilical vein endothelial cell (HUVEC) attachment was assessed in comparison to plastic alone. A 96 well plate was divided such that there were six triplicate time points (0, 0.5, 1, 2, 4, and 6 h) for each treatment. Protoelastin, BSA and fibronectin were added such that each well received 100 μl/10 μg of protein. Plates were stored at 4° C. overnight, to allow adequate coating of the plate surfaces.

The next day, all protein solutions were removed from the wells. Approximately 15,000 HUVEC's were added to each well, except for the zero time point, which received media alone. The DMEM media was supplemented with 20% heat-inactivated human serum, glutamine, penicillin-streptomycin and pyruvate. Plates were incubated at 37° C., with 5% $CO_2$. At each time interval, solution was removed and wells covered with fresh media until the completion of the assay.

At this time, all wells were emptied and washed three times with PBS. The number of adhered cells was determined calorimetrically using One Solution Cell Proliferation Assay (Promega). Each well received 100 μl of fresh media and 20 μl of reagent, before incubation at 37° C., with 5% $CO_2$ for 90 min. Absorbance was read at 490 nm in a plate reader.

Results

Figure 8A:
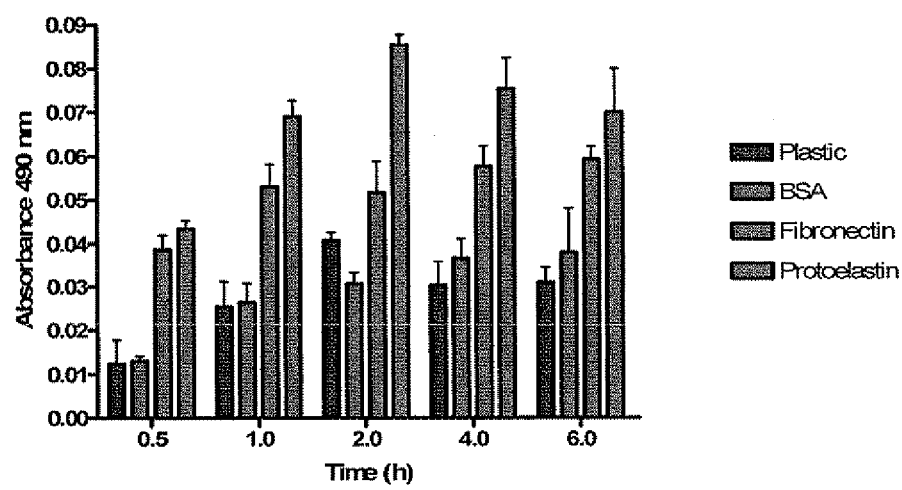
FIG. 8A is a graph of short term (hours) HUVEC attachment and growth (absorbance 490 nm) on tissue culture plastic that was uncoated, coated with BSA, coated with fibronectin, or coated with protoelastin.

Results are shown in FIG. 8A and demonstrate that the HUVECs show superior attachment to a protoelastin coated surface.

EXAMPLE 8

HUVEC Proliferation on Coated Surfaces

Materials and Methods

The effect of protoelastin, fibronectin and bovine serum albumin (BSA), on human umbilical vein endothelial cell (HUVEC) growth was assessed in comparison to plastic alone. A 6 well plate was divided such that there were 3 time points (1, 2 and 3 days) for each treatment. Protoelastin, BSA and fibronectin were added such that each well received 2 ml/200 μg of protein. Plates were stored at 4° C. overnight, to allow adequate coating of the plate surfaces.

The next day, all protein solutions were removed from the wells. Approximately 40,000 HUVEC's were added to each well. The DMEM media was supplemented with 20% heat-inactivated human serum, glutamine, penicillin-streptomycin and pyruvate. Plates were incubated at 37° C., with 5% $CO_2$. At each time interval, solution was removed. Wells requiring further incubation were washed and supplied with fresh media. Wells ready for assay were washed three times with PBS and the number of cells was determined calorimetrically using One Solution Cell Proliferation Assay (Promega). Each well received 100 μl of fresh media and 20 μl of reagent, before incubation at 37° C., with 5% $CO_2$ for 90 min. Absorbance was read at 490 nm in a plate reader.

Results

Figure 8B:
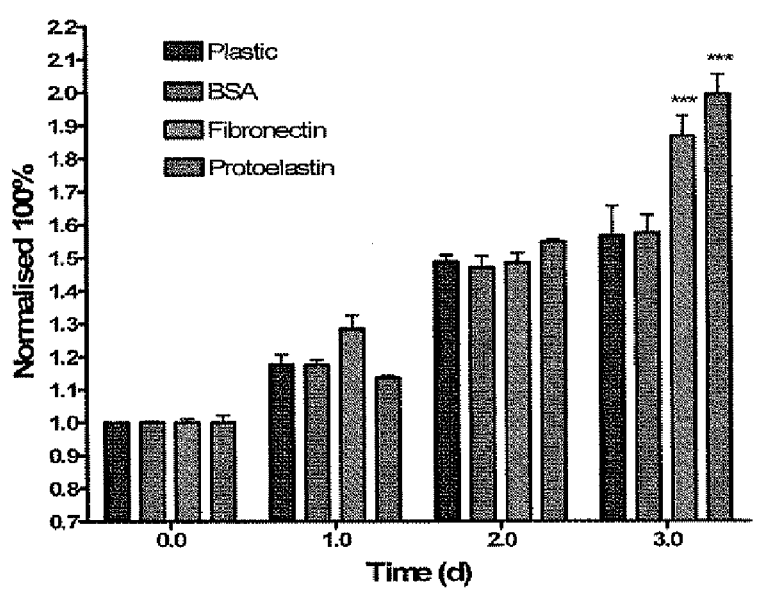
FIG. 8B is a graph of long term (days) growth of HUVECs (absorbance 490 nm) on tissue culture plastic that was uncoated, coated with BSA, coated with fibronectin, or coated with protoelastin.

Results are shown in FIG. 8B, with fibronectin and protoelastin providing the best surface for the proliferation of HUVECs at 3 days.

EXAMPLE 9

Mechanical Property Testing

Materials and Methods

Measurements of tensile strength and Young's Modulus were carried out with an Instron 4302 Computerized Universal Testing Machine. Strips of test material measuring 20 mm wide by 60 mm long were accurately cut. After clamping, the test area was approximately 20 mm×20 mm. Samples were then stretched at a constant rate of 1 mm per minute until break, while force and elongation measurements were recorded. Results were plotted in the form a stress-strain curve and Young's modulus recorded over the initial linear portion of the curve.

Results

Figure 9A:
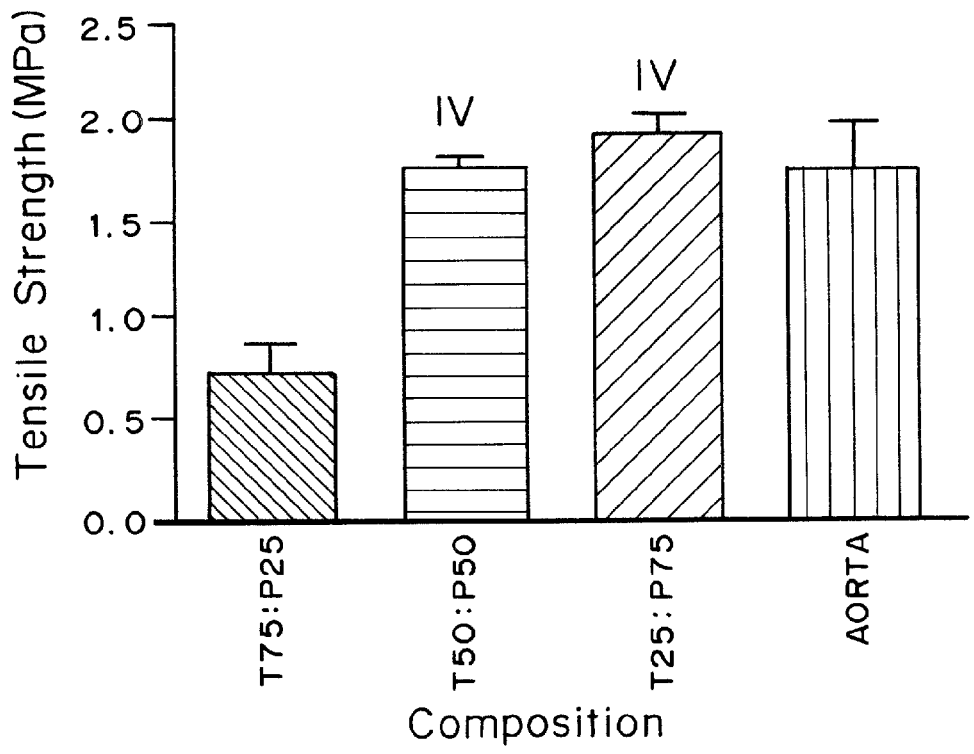
FIGS. 9A and 9B are graphs of the tensile strength (FIG. 9A) and Young's Modulus (elasticity) (FIG. 9B) of three tropoelastin/polycaprolactone composites mixed in different ratios. In each instance they are compared to literature values for human aorta.
Figure 9B:
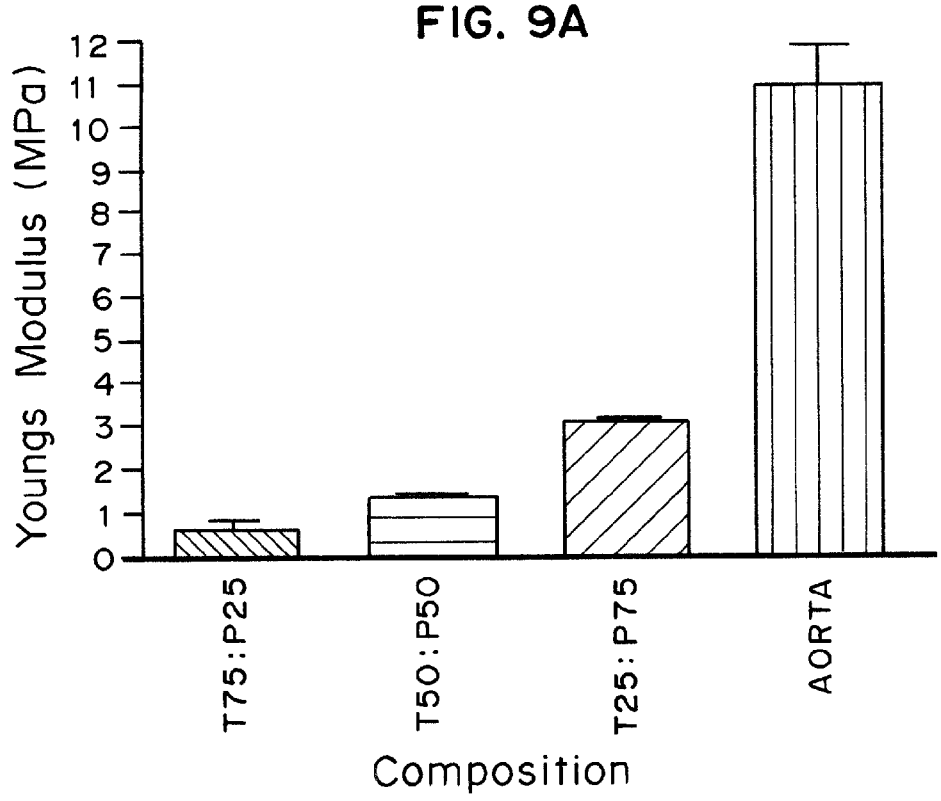

The results are shown in FIG. 9A for tensile strength and FIG. 9B for Young's Modulus (elasticity), showing that the tropoelastin:polycaprolactone 50:50 and 25:75 have a tensile strength comparable to aorta, and that the Young's Modulus increases with increasing polycaprolactone content.

EXAMPLE 10

HUVEC Growth on Protoelastin Based Materials

Materials and Methods

The growth of human umbilical vein endothelial cells (HUVEC) was assessed on electrospun tropoelastin:polycaprolactone composites. A 96 well plate was divided such that the three formulations (100% tropoelastin; 50:50 and 25:75 tropoelastin:polycaprolactone) were observed at 24 and 48 h. Samples of electrospun material were cut into 8 mm circles and pressed into place.

Approximately 30,000 HUVEC's were added to each well. The DMEM media was supplemented with 20% heat-inactivated human serum, glutamine, penicillin-streptomycin and pyruvate. Plates were incubated at 37° C., with 5% $CO_2$. At each time interval, solution was removed. Wells requiring further incubation were washed and supplied with fresh media. Wells ready for assay were washed three times with PBS and the number of cells was determined calorimetrically using One Solution Cell Proliferation Assay (Promega). Each well received 100 μl of fresh media and 20 μl of reagent, before incubation at 37° C., with 5% $CO_2$ for 90 min. Absorbance was read at 490 nm in a plate reader.

Results

Figure 10:
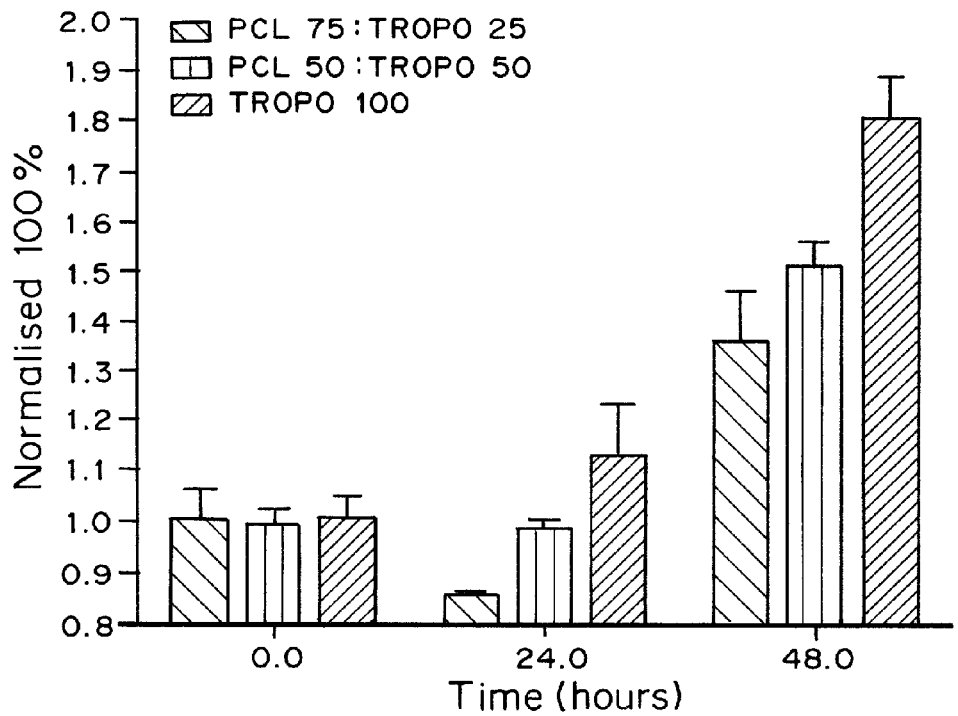
FIG. 10 is a graph of relative growth of Human Umbilical Vein Endothelial Cells on electrospun mats made from tropoelastin and polycaprolactone (PCL:Tropo, 75:25, 50:50, and 100 Tropo), showing that the endothelial cells grow better on surfaces containing increasing amounts of tropoelastin.

The results are shown in FIG. 10. The proliferation of the HUVECs increased dramatically with increasing concentration of tropoelastin.

EXAMPLE 11

Coating of Dacron with Protoelastin

Dacron® was predisposed to bonding with protoelastin according to the method of Phaneuf et al. *J. App. Biomater.* 6, 289-99 (1995). Briefly, Dacron segments were washed in and aqueous Tween 20 solution containing $Na_2CO_3$ for 30 min at 60° C. before rinsing with water. After oven drying, samples were boiled in a 0.5% sodium hydroxide for 30 min, rinsed again with water and dried.

Protoelastin was covalently linked to the treated Dacron® surface using 1-Ethyl-3-[3-dimethylaminopropyl]carbodiimide Hydrochloride (EDC) according to the method of Grabarek and Gergely (1990) Anal Biochem. 185(1):131-5. In a two step reaction, EDC (2 mM) and Sulfo-N-hydroxysuccinimide (Sulfo-NHS) (5 mM) was added to a 100% ethanol solution contain Dacron® samples and reacted for 15 min. 2-mercaptoethanol (final concentration of 20 mM) was added to quench the EDC. Protoelastin was added at an equal molar ratio to the solution and allowed to react for 2 hours at room temperature. The reaction was quenched with the addition of hydroxylamine to a final concentration of 10 mM.

EXAMPLE 13

Attachment of Protoelastin to ePTFE

Materials and Methods

Samples of ePTFE were activated for protein attachment using a plasma modification chamber (Gan et al. (2006) Nuclear Instruments and Methods in Physics Research B, 247. 254-260). Briefly, from this protocol, plasma treatments were carried out in nitrogen gas at a pressure of 2×10-3 Torr. The forward power used in the chamber was 100 W with a reverse power of 12 W when matched. Plasma immersion ion implantation (PIII) with high voltage pulse bias of 20 kV and 20 μs duration at a frequency of 50 Hz was used for more intense modification of the surface. Samples were reacted within the chamber for a period of 800 seconds for either plasma or PIII modification.

Treated materials were punched into 10 mm circles and incubated with a 1 mg/ml tropoelastin solution overnight at 37° C. No additional cross-linking agent was necessary for the formation of covalent linkages. Tropoelastin coated samples were then washed three times with PBS and blocked with a 10 mg/ml BSA solution for 1 h at room temperature. At this time, a subset of samples from each treatment was boiled in 5% SDS for 10 mins. Samples were then washed again with PBS before treatment with 1 ml of monoclonal anti-elastin antibody (primary) and incubated for 1 h at room temperature. Following PBS washing, 1 ml of HRP mouse antibody (secondary) was added before a second incubation period. Finally, 1 ml of (2,2'-azino-bis(3-ethylbenzthiazoline-6-sulphonic acid) ABTS solution was supplied to each sample and the absorbance at 405 nm read after 1 h at 37° C. Absorbance is expressed relative to tropoelastin-free controls.

Results

Figure 11:
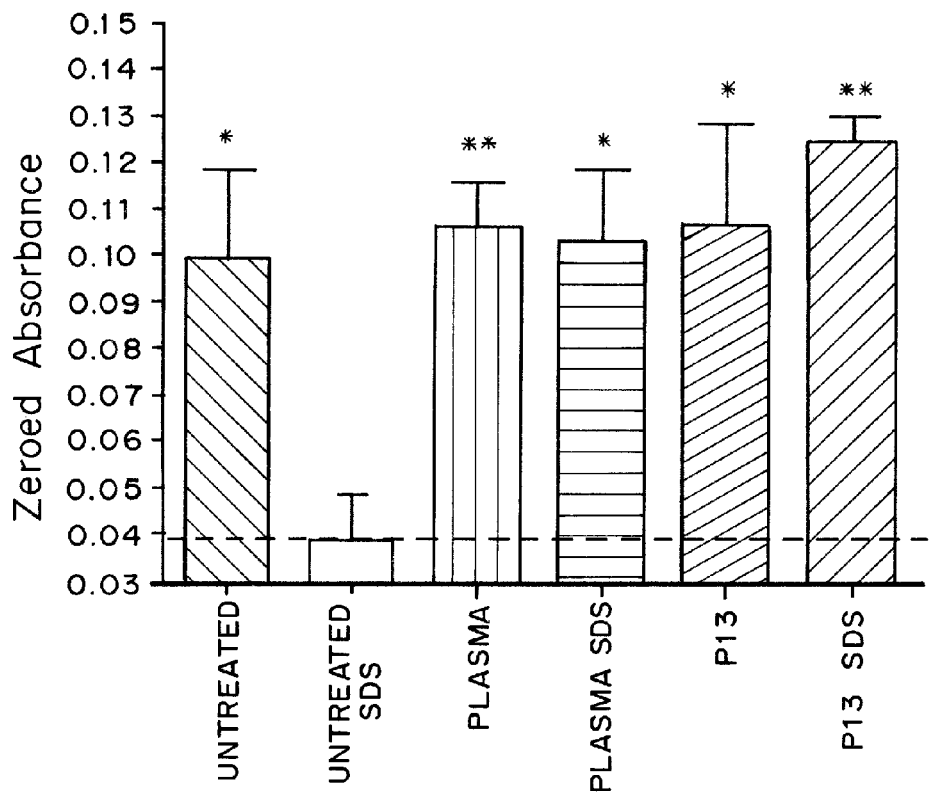
FIG. 11 is a graph of relative adhesion of tropoelastin to ePTFE after no treatment, plasma treatment or PIII treatment.

FIG. 11 shows the amount of tropoelastin retained on ePTFE after no treatment, plasma treatment or PIII treatment. In each case, a no wash case is compared to boiling in SDS. On untreated ePTFE, SDS washing removes all of the protein, given that no permanent bonds are formed, in contrast to the plasma and PIII cases, where the SDS washed samples are not significantly different from their pre-wash controls.

EXAMPLE 14

Biocompatibility

Materials and Methods

Cellular responses to cross-linked tropoelastin were assessed 13 weeks after implantation in the dorsum of male guinea pigs, with collagen implants used as a control.

Results

Both cross-linked tropoelastin and collagen elicited a similar cell mediated response to the presence of a foreign body. "The observed cellular infiltrates did not suggest the presence of a specific immunological reaction. The collagen control had a short-lived duration following implantation and was largely dispersed by week four. The cross-linked tropoelastin samples were uniformly surrounded by fibrous encapsulation with minimal to moderate inflammation"

Modifications and variations of the present invention will be obvious to those skilled in the art from the foregoing detailed description and are intended to come within the scope of the appended claims. References cited herein are specifically incorporated by reference.

We claim:

1. A composition comprising protoelastin made from human recombinant tropoelastin,
   wherein the human recombinant tropoelastin is selected from the group consisting of
   full length tropoelastin;
   one or more splice variants of tropoelastin selected from the group consisting of an isoform lacking domains 22 and 26A and an isoform lacking domain 22 but including domain 26A;
   chemically modified tropoelastin selected from the group consisting of acetylated tropoelastin, pegylated tropoelastin, tropoelastin having a chemical or peptide linker bound thereto, and methylated tropoelastin; and
   recombinant tropoelastin fragments selected from the group consisting of a fragment encompassing the N-terminus domain but not all of the C-terminus domain, a fragment not encompassing all of the N-terminus domain or C-terminus domain, a fragment encompassing the C-terminus domain but not all of the N-terminus domain, and a fragment encompassing domain 36;
   wherein the protoelastin is made by
   (a) covalently binding tropoelastin to a metal, ceramic, bone, or polymeric substrate;
   (b) laminating tropoelastin to a synthetic non-natural polymer to form a tropoelastin-polymer laminate;
   (c) blending tropoelastin with a synthetic non-natural polymer; or
   (d) a combination thereof.

2. The composition of claim 1, further comprising a human recombinant tropoelastin selected from the group consisting of
   tropoelastin including all 36 domains expressed by the elastin gene;
   an isoform lacking domains 22 and 26A; an isoform lacking domain 22 but including domain 26A;
   a fragment encompassing the N-terminus domain but not all of the C-terminus domain;
   a fragment encompassing the C-terminus domain but not all of the N-terminus domain; and
   a fragment encompassing domain 36.

3. The composition of claim 1, wherein the chemically modified tropoelastin is selected from the group consisting of acetylated tropoelastin, pegylated tropoelastin, tropoelastin having a chemical or peptide linker bound thereto, and methylated tropoelastin.

4. The composition of claim 1, having a mechanical tensile strength of greater than 1 MPascal, greater than 2 MPascal or greater than 3 MPascal.

5. The composition of claim 1, comprising a cell culture substrate, wherein the protoelastin is present as a coating.

6. The composition of claim 1, further comprising at least one therapeutic, prophylactic or diagnostic agent.

7. The composition of claim 1, in the form of a vascular implant, medical implant, or prosthesis.

8. The composition of claim 1, wherein the human recombinant tropoelastin is covalently bound or tethered to a substrate which has been surface activated.

9. The composition of claim 1, wherein the protoelastin comprises a laminate having an exterior surface of human recombinant tropoelastin, on one or more layers of the synthetic non-natural polymer.

10. The composition of claim 1, wherein the protoelastin comprises a laminate of alternating human recombinant tropoelastin and synthetic non-natural polymer, with one or more layers of the polymer between the layers of the human recombinant tropoelastin, and wherein there is one or more types of polymer.

11. A device comprising protoelastin formed as a component of a vascular conduit, a stent, a stent-graft, a vascular scaffold, a surgically or percutaneously implantable heart valve, a vascular/septal occlusion device, a vascular closure device, or as a surface coating for a vascular device or implant.

12. A device comprising protoelastin formed into a matrix for engineering cartilage, bone, tendon or ligament implant, pin, rivet, screw, rod, artificial knee, elbow or other joint, intervertebral disk, or surface thereof wherein the implant interfaces with the host tissue.

13. The composition of claim 1, wherein the protoelastin is a blend of human recombinant tropoelastin and one or more synthetic non-natural polymers.

14. The composition of claim 1, wherein the protoelastin is crosslinked.

15. The composition of claim 1, wherein the protoelastin is formed by electrospinning of human recombinant tropoelastin.

16. A method of making a biomaterial with desired mechanical properties comprising:
   (A) providing a composition comprising protoelastin made from human recombinant tropoelastin, wherein the human recombinant tropoelastin is selected from the group consisting of
   (i) full length human tropoelastin;
   (ii) one or more splice variants of human recombinant tropoelastin selected from the group consisting of an isoform lacking domains 22 and 26A, and an isoform lacking domain 22 but including domain 26A;
   (iii) chemically modified tropoelastin selected from the group consisting of acetylated tropoelastin, pegylated tropoelastin, tropoelastin having a chemical or peptide linker bound thereto, and methylated tropoelastin; and
   (iv) recombinant tropoelastin fragments selected from the group consisting of a fragment encompassing the N-terminus domain but not all of the C-terminus domain, a fragment not encompassing all of the N-terminus domain or C-terminus domain, a fragment encompassing the C-terminus domain but not all of the N-terminus domain, and a fragment encompassing domain 36,
   wherein the human recombinant tropoelastin is made by
   (a) covalently binding the tropoelastin to a metal, ceramic, bone, or polymeric substrate;
   (b) laminating the tropoelastin to a synthetic non-natural polymer;
   (c) blending the tropoelastin with a synthetic non-natural polymer; or
   (d) combinations thereof; and
   B) adjusting the composition of tropoelastin, the covalent binding of the tropoelastin to a surface, or the crosslinking of the tropoelastin to produce the biomaterial with desired mechanical properties.

17. The method of claim 16, comprising forming the biomaterial by electrospinning.

18. The method of claim 16, wherein the protoelastin is formed by laminating a synthetic non-natural polymer and tropoelastin.

19. The method of claim 16, wherein the protoelastin is formed by blending tropoelastin with a synthetic non-natural polymer.

20. The method of claim 17, wherein the protoelastin has a tensile strength range of greater than 1 M Pascal and was made by forming a polymer blend or polymer laminate with human recombinant tropoelastin.

21. The method of claim 20, further comprising crosslinking the tropoelastin to itself or to the polymer.

22. The method of claim 16, further comprising at least one therapeutic, diagnostic or prophylactic agent.

* * * * *

UNITED STATES PATENT AND TRADEMARK OFFICE
CERTIFICATE OF CORRECTION

| | | |
|---|---|---|
| PATENT NO. | : 7,700,126 B2 | |
| APPLICATION NO. | : 11/864006 | |
| DATED | : April 20, 2010 | |
| INVENTOR(S) | : Martin Kean Chong Ng, Anthony Steven Weiss and Steven Garry Wise | |

It is certified that error appears in the above-identified patent and that said Letters Patent is hereby corrected as shown below:

Claim 20, column 22, line 34, replace "claim 17" with --claim 16--.

Signed and Sealed this
Tenth Day of May, 2011

David J. Kappos
*Director of the United States Patent and Trademark Office*